United States Patent [19]

Jackson

[11] 4,256,225
[45] Mar. 17, 1981

[54] FIBEROPTIC ENDOSCOPE ACCESSORY INSTRUMENT STORAGE CASE

[76] Inventor: Frank W. Jackson, Twillingate, R.D. 3, Mechanicsburg, Pa. 17055

[21] Appl. No.: 61,947

[22] Filed: Jul. 30, 1979

[51] Int. Cl.³ .................... B65D 85/02; B65D 83/00
[52] U.S. Cl. .................................. 206/303; 206/363; 206/409; 206/459; 220/19
[58] Field of Search ............... 206/303, 409, 459, 314, 206/387, 363; 220/19, 22, 94 R; 128/6

[56] References Cited

U.S. PATENT DOCUMENTS

| | | | |
|---|---|---|---|
| 2,518,081 | 8/1950 | Sharaf | 220/19 |
| 2,579,131 | 12/1951 | Tinsley | 206/409 |
| 3,351,209 | 11/1967 | Kofoed et al. | 206/459 |
| 3,759,395 | 9/1973 | Jublin | 220/22 |
| 3,948,251 | 4/1976 | Hosono | 128/6 |

Primary Examiner—William T. Dixson, Jr.
Attorney, Agent, or Firm—Eugene Chovanes; Edward Lovett Jackson

[57] ABSTRACT

A flat, rectangular case for storing a lengthy flexible endoscopic accessory instrument when the instrument is not being used. The various instruments, which are in the form of thin flexible cables up to seven feet long, having a linear bias, are stored individually, in the case, in a coiled state. The natural bias of the instrument serves to position and secure the instrument within the case. The instruments can be readily inserted into, and withdrawn from, the case through an opening in the side wall. A plurality of cases can be supported adjacent one another in a rack.

1 Claim, 7 Drawing Figures

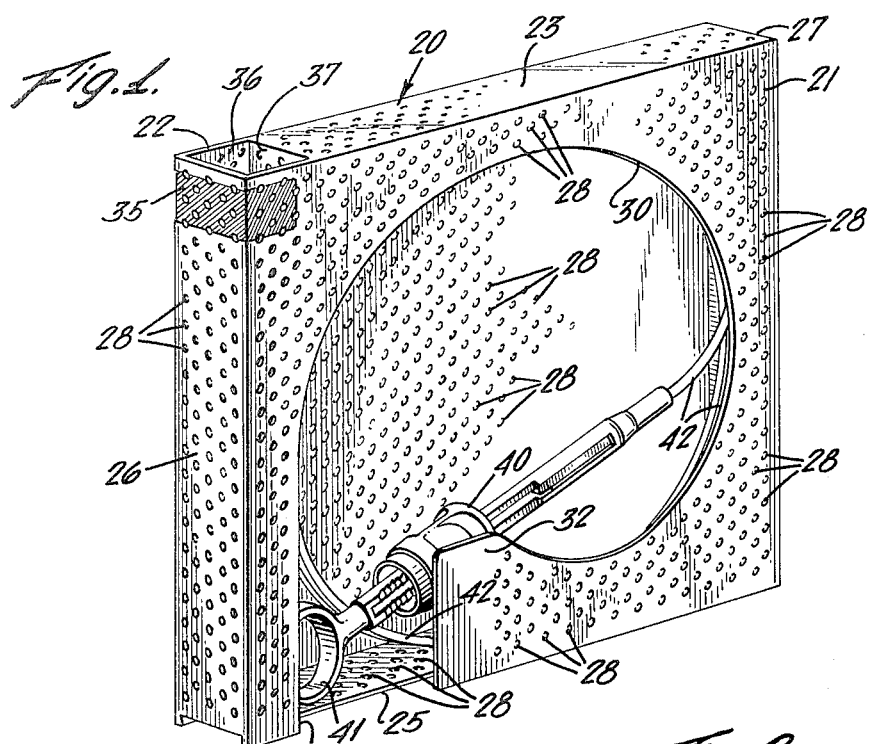
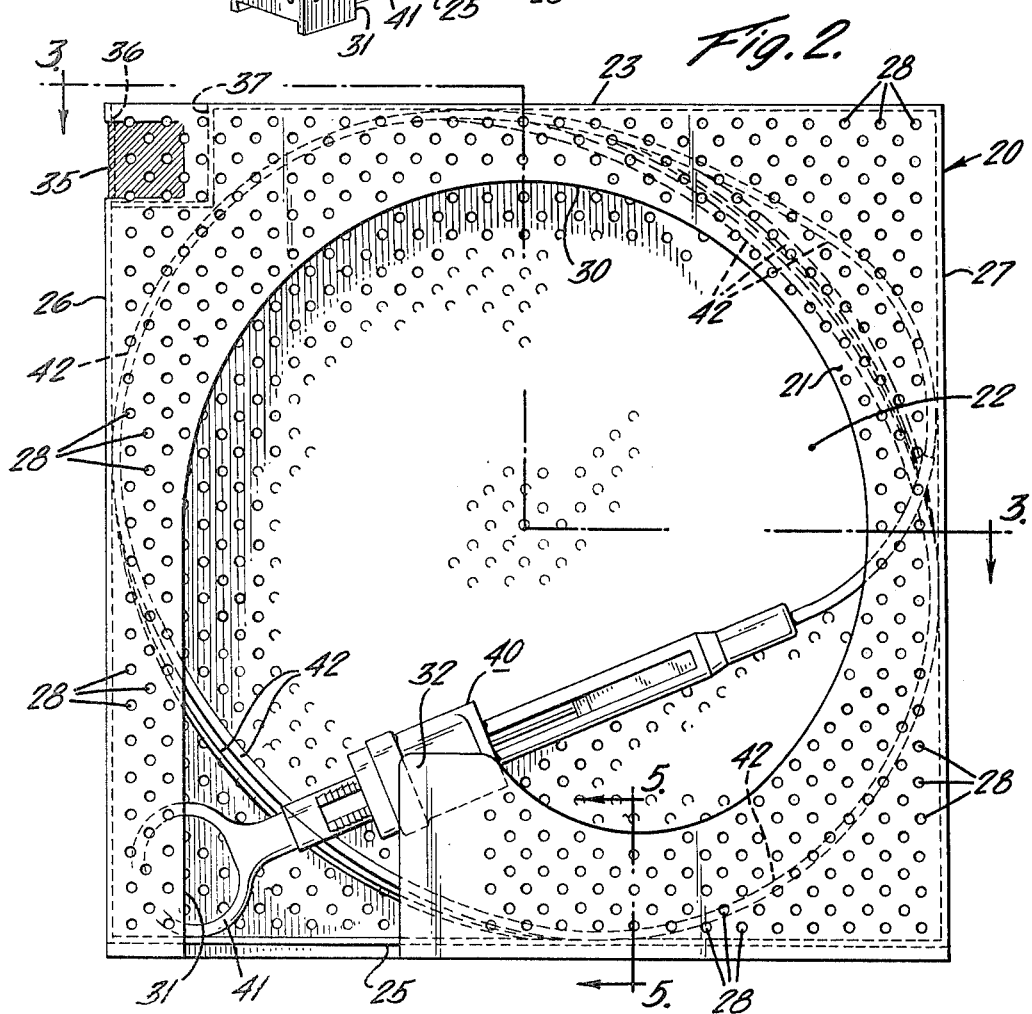

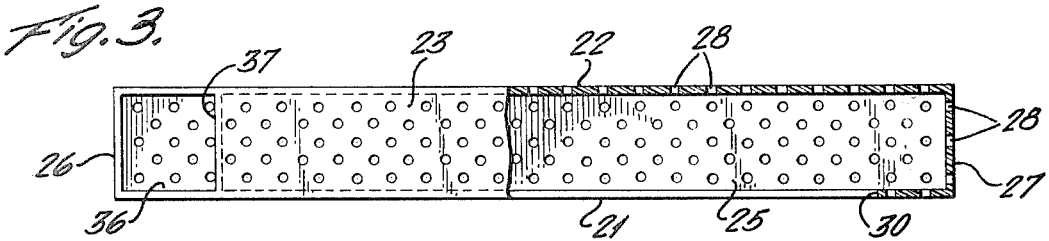
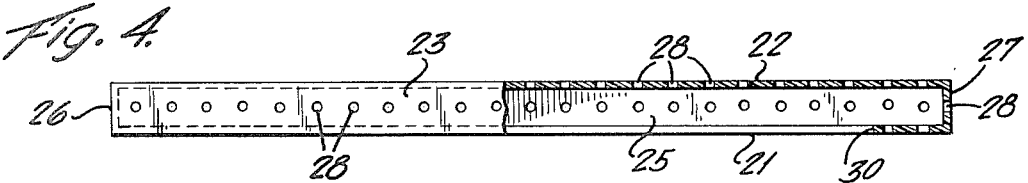
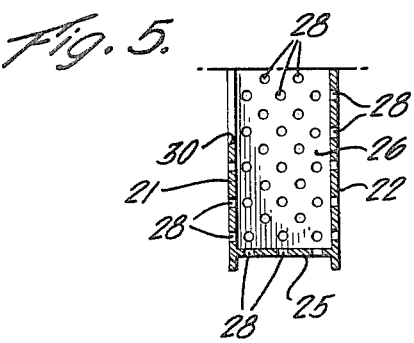
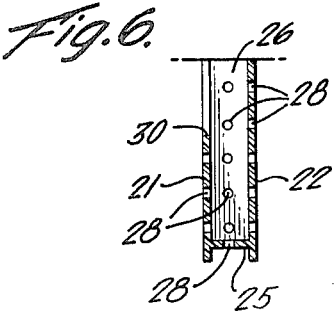
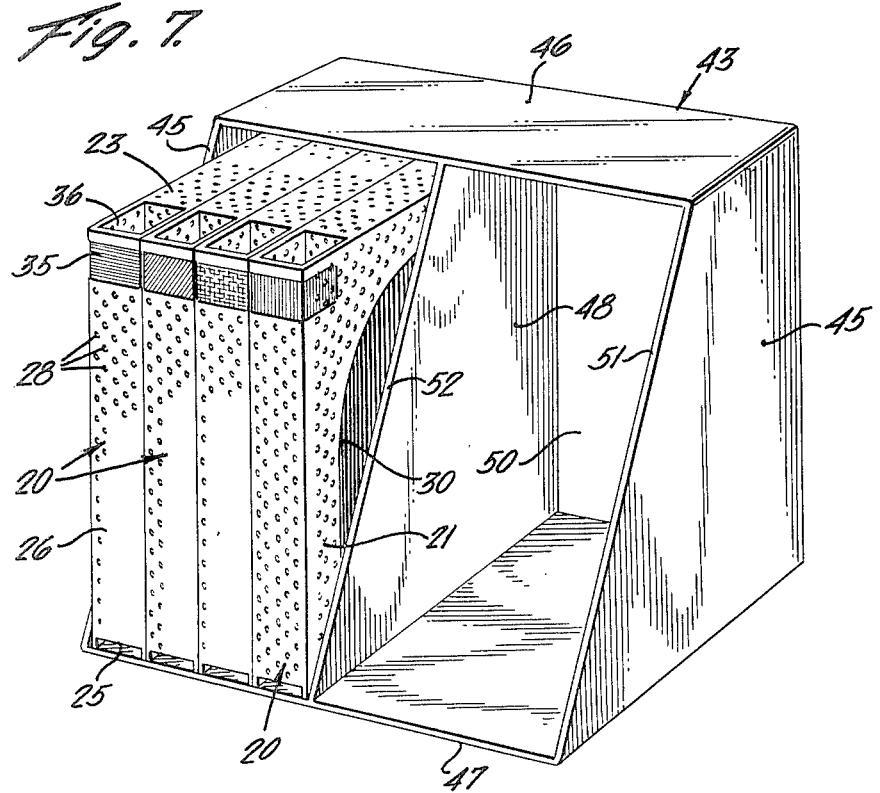

FIBEROPTIC ENDOSCOPE ACCESSORY INSTRUMENT STORAGE CASE

BACKGROUND OF THE INVENTION

Fiberoptic endoscopy is used in human medicine in the field of gastroenterology and pulmonary disease. The fiberoptic endoscope permits the operator to see and work within the human body without having to cut into the body from outside. A fiberoptic endoscope is essentially a long flexible conduit having parallel, adjacent channels or tubes. The endoscope, or flexible conduit is inserted into the body through, for instance, the mouth opening. Some of the tubes within the conduit contain treated spun glass fibers through which light can be transmitted around bends. Suction, air and water can be applied through other channels. Additionally, a tube or channel within the endoscope can receive any one of a variety of accessory instruments. These accessory instruments consist essentially of a thin long flexible cable up to seven feet in length, having a forward, or tip, end to be inserted into the body and an end which remains outside the body. A wide assortment of accessory instruments is now available to biopsy, wash, brush, coagulate, snare, cut, and retrieve various lesions and conditions. The tip end of the instruments may have mechanisms operated from a handle at the opposite end. Such mechanisms include, variously, biopsy forceps, scissors, brushes, snares, catheters, clamps and other mechanisms.

The accessory instruments are inserted and used selectively in the endoscope, and when not in use are stored outside the instrument.

The present methods of accessory instrument storage are makeshift systems which are merely developed by the medical assistants in each laboratory. These are usually either one of two types.

In the first type, the equipment is simply hung from wall pegs. This method has several disadvantages including sloppy housekeeping, tangling of instruments, breakage of tips, and difficulty in finding the proper instrument in a dimmed endoscopic operating room. Furthermore, the accessory instruments are difficult to transport and must be loosely coiled up on the portable endoscopy cart.

In the second storage method generally used, the accessories are coiled and enclosed in manilla or plastic envelopes. This has the disadvantage of great difficulty in finding the appropriate instrument during an endoscopic examination in a dimmed room. Additionally, there is no ability for the equipment to air-dry. Also, there is tattering of the manilla envelope or the polyvinyl envelope, and breakage of the equipment.

The average cost of each accessory instrument is very high. The accessories are delicate and fragile instruments with high breakage and replacement rate. The typical gastrointestinal endoscopic suite has thousands of dollars invested in accessory instruments, with a substantial annual replacement and repair cost. Yet, the equipment is stored by methods which are most inefficient and, as noted, such methods contribute significantly to equipment deterioration and breakage.

SUMMARY OF THE PRESENT INVENTION

The present invention provides a solution to the above detailed problems, and substantially eliminates breakage and deterioration of the accessory instruments. It removes the frustration of retrieving the accessory instruments, and replacement of these accessory instruments, to and from storage during the performance of endoscopy.

The device consists essentially of a flat rectangular shape case, having one of the flat walls extending continuously, and the opposite flat wall having therein a large generally circular shape opening. The circular shape opening permits a relatively tightly coiled accessory unit to be inserted into the case through the circular opening, after which the coiled accessory instrument is allowed to naturally expand into a larger coil whereby the instrument is held firmly but delicately within the container. The coil expands because the natural bias of the instrument is toward a straight relaxed position.

The case has a slot in the flat wall adjacent the circular opening, which receives the handle of the stored accessory instrument. The coiled accessory instrument is thus stored and secured in a fixed and firm position.

The accessory instrument is removed from the case by simply grasping the instrument through the circular opening, and flexing it to bring it out of the case, through the opening.

Perforated walls in the case permit complete air flow within the case for complete air drying of the accessory instrument. The bottom of the case is raised slightly to allow air flow through the unit from top to bottom.

The open slot at the side of the circular opening allows for easy grasping and removal of the accessory instrument through the circular opening.

A raised tab acts to hold the handle of those accessory instruments that have handles.

The case may optionally be provided with an area for color coding labels for each instrument. This color system provides a quick method for identifying the location of any desired accessory instrument during the course of an endoscopic examination.

A recessed area at the top edge allows for finger insertion and removal of the case when a plurality of units are stored vertically as in a book rack.

DESCRIPTION OF THE DRAWINGS

FIG. 1 is a perspective view of a storage case of the invention showing an endoscopic accessory instrument stored within the case.

FIG. 2 is a right side elevation of the case of FIG. 1.

FIG. 3 is a plan view of the case shown in FIG. 2 and taken on the stepped line 3—3 of FIG. 2. The upper left portion of the case is shown in full top plan view and the right side is shown as a sectional plan view through the case. Also, the endoscope accessory instrument has been removed for clarity.

FIG. 4 is a view similar to FIG. 3 showing a case of identical design, but of a greatly reduced width. Such a case is used in the storage of accessory instruments whose terminal ends are smaller than those on the instruments shown in FIG. 1.

FIG. 5 is a fragmentary transverse sectional view taken on the line 5—5 of FIG. 2.

FIG. 6 is a view similar to FIG. 5 but of a case having a greatly reduced width as shown in FIG. 4.

FIG. 7 is a perspective view of the entire system of my invention and shows a number of cases containing accessory instruments color-coded for ease of identification, neatly arranged within a carrier rack that can be wall-mounted or desk-mounted, and designed for the easy removal of the desired case by way of the finger hole provided within the case and the open design of the carrier rack itself.

DESCRIPTION OF THE PREFERRED EMBODIMENT

A storage case 20 as seen in perspective in FIG. 1 has side walls 21 and 22 connected by a top wall 23, bottom wall 25 and opposing end walls 26 and 27. Opposing walls are parallel. The container is in the form of a flat rectangular shape, wherein the surfaces of side walls 21 and 22 are distinctly greater than the surfaces of the ends walls 26 and 27, or the top and bottom walls 23 and 25. A typical case could be for instance ⅜" wide for accessory instruments such as catheters and brushes which have no wide parts, or 1½" wide for those with forceps or snare handles. The case may have a height of 8 to 10", for instance, and a depth of 8 to 10".

For purposes of this description, the case will be referred to in terms of a vertically disposed case for vertical storage, but it should be understood that the cases can be stored optionally horizontally, if desired.

The case is made of, desirably, a suitable lightweight chemically inert plastic whereby the containers can be chemically, gas, or heat sterilized. The walls of the case have a plurality of perforations 28, for instance, of a 1/16" diameter on ½" centers.

The side wall 21 has a substantial opening 30 desirably circular, of for instance a 9" diameter. The circular opening 30 has a slot 31 which is formed adjacent, and continuous with, the circular opening 30. Slot 31 may desirably extend tangentially from the circular opening 30.

Bottom wall 25 is slightly raised above the bottom surface of wall 21, to allow for air flow through the unit from top to bottom. A raised tab 32 which is formed by the position of slot 31 and circular opening 30 acts to hold the handle of some accessories for easy grasp for removal of the accessory instruments.

There may optionally be formed a slightly depressed area 35 which runs across the front wall 26 and a portion of the side walls 21 and 22, at the top of the case to provide an area for color coding labels for each instrument. For instance, colored tabs can be adhesively secured in this depressed area 35 wherein red can be used for instance for a biopsy accessory, orange can be used for a cytology brush, green for a polypectomy snare, blue could be used for a foreign body retriever, gray for a coagulating catheter, and white for a miscellaneous accessory instrument.

An optional recessed area 36 which can be in the form of a rectangular opening in top wall 23 with an inner wall 37 allows for finger insertion and removal of the storage case 20 when units are stored vertically as in a book rack.

In use, the endoscopic accessory instrument is coiled outside the storage case in preparation for storage. As indicated above, such accessory instrument consists essentially of a flexible cable portion of up to seven feet in length, having a bias toward a straight line in a relaxed position. Of course, the cable is quite flexible for use in being threaded through various body openings so the cable can be readily coiled in preparation for storage. A flexible cable of for instance seven feet in length, can be readily coiled into a circular coil of for instance 6" in diameter. The various accessory instruments have at the tip end of the cable, for instance, a snare, or a retriever, or an injection needle, or electrodes or brushes. At the opposite end of the cable there is a handle or operating portion with a plunger or trigger device and a housing which slidably supports the plunger or trigger which in turn is connected through the cable portion to the snare or brush or the like. The coiled accessory instrument is inserted through opening 30 into the storage case as seen in FIGS. 1 and 2. The handle portion including housing 40 and trigger or plunger 41 is positioned at tab 32 and slot 31. The cable portion 42 is then allowed to expand and the accessory instrument seeks to uncoil and reach a longitudinal linear straight position. However, the restraining influence of the case including the bottom and top walls, 23 and 25, the front and back walls 26 and 27, and the side walls 21 and 22 restrain the accessory instrument into a coil which conforms to the inner confines of the case. Thus the accessory instrument itself, with its inherent springiness, serves to act as the positioning and containing element in keeping the accessory instrument securely held within the storage container. Side wall 21 which surrounds the circular opening 30 and slot 31 adequately aids in keeping the coil positioned, notwithstanding that the relatively large opening 30 is used for ready insertion of the instrument into the storage case.

To remove the accessory instrument from the storage unit it is merely necessary to grasp the plunger 41 and housing 40 as well as the cable 42 and flex them so that the flexible coiled cable is first somewhat distended for initial removal through the circular opening 30. Since the accessory cable 42 is very flexible no problem is encountered in removing the accessory instrument through the circular opening. The accessory instrument is then taken to the endoscope for use as desired.

The unit 20 can then selectively or optionally be placed into rack 43 as seen in FIG. 7 which holds a plurality of cases 20 much as books are held in a book rack.

Rack 43 has sides 45, a top 46, bottom 47 and an internal upright divider 48, along with a back wall 50. The front edges 51 of wall 45 and front edge 52 of wall 48 is desirably slanted so that, while the individual cases 20 are securely held in the rack, an individual case 20 can be selectively and conveniently removed with no interference from rack 43. A user merely inserts his finger through opening 36 in the desired case identified by a suitable color at 35, and removes case 20 from rack 43. Replacement of case 20 and the rack 43 can be just as easily accomplished.

Where the accessory instrument does not have a handle, storage of the instrument in the case is virtually identical to that described above except there is no need to position the handle in the slot location 31.

When necessary to sterilize the accessories, the entire storage case 20, with the accessory instrument positioned therein, can be place in a suitably sterilized bath or atmosphere. Since the case material is of an inert nature, there is no destruction of the case by the sterilization process. The case itself has the advantage of being sterilized along with the accessory instrument so a desirable condition is achieved.

In view of my invention and disclosure, variations and modifications to meet individual whim or particular need will doubtless become evident to others skilled in the art, to obtain all or part of the benefits of my invention without copying the structure shown, and I therefore claim all such insofar as they fall within the reasonable spirit and scope of my claims.

What I claim as new and desire to secure by Letters Patent is:

1. A fiberoptic endoscope accessory instrument having
  (a) a thin, long, flexible, substantially straight portion capable of being coiled into circular form, the flexible portion being biased toward the substantially straight relaxed position from the circular form;
  (b) an operating end at one end of the flexible portion; and
  (c) a tip end on the flexible portion opposite the operating end;
in combination with an accessory instrument storage case in the form of a flat rectangular-shape having
  (a) opposing side walls on the flat side of the case with one of the case side walls having a central circular opening with a slot adjacent to, and integral with, the circular opening;
  (b) opposing end walls on the front and back of the case;
  (c) a top and bottom wall; and
  (d) the walls of the case perforated;
wherein
  (a) the accessory instrument is coiled into circular form outside the case to a diameter substantially the same as the circular opening in the case, with the operating end at one point in the coil and the tip at another point in the coil;
  (b) the coiled instrument is inserted into the case, and subsequently withdrawn from the case, by a person grasping the coil at the point on the coil where the handle is located;
  (c) the point on the coil where the handle is located being positioned within the case at the location of the slot in the side wall;
  (d) the instrument is stored within the case in coiled form;
  (e) the instrument seeks to expand when it is within the case, from the coiled form to a straight position; and
  (f) the case restrains the coiled instrument from expanding whereby the walls of the case secure the instrument within the case.

* * * * *